US005811372A

United States Patent [19]

Riggle et al.

[11] Patent Number: 5,811,372
[45] Date of Patent: Sep. 22, 1998

[54] METHOD OF CONTROLLING SPROUT FORMATION IN POTATOES BY SELECTIVE APPLICATION OF CHLORPROPHAM, CARVONE, BENZOTHIAZOLE AND ETHYLENE

[75] Inventors: Bruce D. Riggle, Eaton, Colo.; Ronald K. Schafer, Boise, Id.

[73] Assignee: Platte Chemical Company, Greeley, Colo.

[21] Appl. No.: 859,866

[22] Filed: May 21, 1997

[51] Int. Cl.$^6$ .......................... A01N 31/06; A01N 43/78; A01N 47/10
[52] U.S. Cl. ............................................. 504/138; 504/143
[58] Field of Search ..................................... 504/138, 143

[56] References Cited

U.S. PATENT DOCUMENTS

| | | | |
|---|---|---|---|
| 2,341,868 | 9/1944 | Hitchcock et al. | 47/58 |
| 2,837,570 | 6/1958 | Linder et al. | 260/587 |
| 3,128,170 | 4/1964 | Plant | 71/26 |
| 4,078,480 | 3/1978 | Luck | 99/476 |
| 4,226,179 | 10/1980 | Sheldon, III et al. | 99/475 |
| 4,532,156 | 7/1985 | Everest-Todd | 427/220 |
| 4,564,718 | 1/1986 | Still et al. | 585/310 |
| 4,735,134 | 4/1988 | Brouwer | 99/476 |
| 4,857,345 | 8/1989 | Sardo | 426/310 |
| 4,887,525 | 12/1989 | Morgan | 99/476 |
| 4,977,825 | 12/1990 | Morgan | 99/476 |
| 5,009,152 | 4/1991 | Morgan | 99/476 |
| 5,129,951 | 7/1992 | Vaughn et al. | 71/122 |
| 5,139,562 | 8/1992 | Vaughn et al. | 71/88 |
| 5,308,871 | 5/1994 | Chastain et al. | 514/690 |
| 5,436,226 | 7/1995 | Lulai et al. | 504/291 |
| 5,580,596 | 12/1996 | Winkelmann et al. | 426/321 |

FOREIGN PATENT DOCUMENTS

| | | |
|---|---|---|
| 8652829 | 1/1985 | Australia . |
| 1 203 394 | 4/1986 | Canada . |
| 0 394 961 A2 | 10/1990 | European Pat. Off. . |
| 0 394 961 A3 | 5/1991 | European Pat. Off. . |
| 63-179801 | 1/1987 | Japan . |
| WO 88/08249 | 11/1988 | WIPO . |
| WO 93/06724 | 4/1993 | WIPO . |

OTHER PUBLICATIONS

J.L. Beveridge, et al., "The Assessment of Some Volatile Organic compounds as Sprout Suppressants for Ware and Seed Potatoes (abstract)", Potato Research, 1981, University of Glasgow, Glasgow, UK.

Prange, Robert, et al, "Ethylene as a Sprout Control Agent in Stored Russet Burbank Potatoes (abstract)", 81$^{st}$ Annual Meeting of the Potato Association of America, Aug. 3–7, 1997, Prince Edward Island, Canada.

Wang, et al, "Effects of Ethylene on Respiration and Sugar content of Russet Burbank and Shepody Potatoes (abstract)", 81$^{st}$ Annual Meeting of the Potato Association of American, Aug. 3–7, 1997, Prince Edward Island, Canada.

Kalt, et al, "Efficacy of Novel Sprout Inhibitors for Stored Russet Burbank Potatoes (abstract)", 81$^{st}$ Annual Meeting of the Potato Association of American, Aug. 3–7, 1997, Prince Edward Island, Canada.

Wang, et al, "Ethylene Contamination During CIPC Application Increases Respiration and Sugars of Stored Potatoes (abstract)", 81$^{st}$ Annual Meeting of the Potato Association of American, Aug. 3–7, 1997, Prince Edward Island, Canada.

Daniels–Lake, B.J., et al., "The Effects of Ozone and 1,8–Cineole on Sprouting, Fry Color and Sugars of Stored Russet Burbank Potatoes," American Potato Journal, vol. 73, 1996, pp. 469–481.

Vaughn, Steven F., et al., "Volatile Monoterpenes Inhibit Potato Tuber Sprouting," American Potato Journal, 1991, vol. 68, 1991, pp. 821–831.

Vaughn, Steven F., et al., "Naturally–Occuring Aromatic Compounds Inhibit Potato Tuber Sprouting," American Potato Journal, vol. 70, 1993, pp. 527–533.

Kleinkopf, G.E., et al., "CIPC Residues on Stored Russet Burbank Potatoes: I. Maximum Label Application," American Potato Journal, vol. 74, 1997, pp. 107–117.

Orr, Paul, et al., "Seeking Biological Sprout Control in Long–Term Storage," Valley Potato Grower, Jul. 1995, p. 31.

Lewis, Mike, et al., "Research Continues on Natural Inhibitors," Potato Grower of Idaho, pp. 20–21, Jul. 1993.

Shetty, Kiran K., et al., "Fine–Tuning Time for Inhibition," Potato Grower of Idaho, Dec. 1993, pp. 14–15.

Shetty, Kiran K., et al., "Controlling Potato Sprouting is Most Important Factor—Applications Vital," Potato Grower of Idaho, Sep. 1995, pp. 18–19.

Kleinkopf, Gale, et al., "CIPC Application to Potatoes in Long–Term Storage Examined," Potato Country, Feb. 1996, pp. 24–26.

"Clean Crop Sprout NIP® 7A Sprout Nip," 1994 Specimen Label and Material Safety Data Sheet, Platte Chemical Co., 50 S. Main Street, Freemont, NE 68025–5667.

"Clean Crop Sprout NIP® Emulsifiable Concentrate," 1994 Speciman Label and mateial Safety Data Sheet, Platte Chemical Co., 50 S. Main Street, Fremont, NE 68025–5697.

*Handbook of Plant and Crop Physiology*, Pessarakli, M., ed., Chapter 20, Dennis, Frank G., Jr., Dormancy: Manifestations and Causes, pp. 448–450, 1995.

(List continued on next page.)

*Primary Examiner*—S. Mark Clardy
*Attorney, Agent, or Firm*—Carol W. Burton, Esq.; Holland & Hart LLP

[57] ABSTRACT

A method of controlling sprout formation in tubers includes application of CIPC and carvone or application of CIPC and benzothiazole and then storing the treated tubers. In a preferred embodiment of the method, tubers to be placed in storage are treated with a composition of CIPC and carvone or CIP and benzothiazole utilizing thermal fogging techniques, with the average effective residue of CIPC on the tubers of approximately 16.6 ppm. When the tubers are to be used to growth tuber-producing plants, for example, when the tubers are to be used as seed potatoes, after removal from storage, the seed potatoes are treated with ethylene at planting, thereby stimulating sprout growth.

7 Claims, No Drawings

OTHER PUBLICATIONS

Oosterhave, K., et al., Comparative study on the action of S–(+)–carvone, in situ, on the potato storage fungi *Fusarium solani* var. *coeruleum* and *f. sulphureum,* Journal of Applied Bacteriology, 1996, 80, 535–39.

Abeles, Frederick B. "Growth and Development Effects of Ethylene", Chapter 6 in Ethylene in Plant Biology, Academic Press, NY. pp. 103–107, 1973.

Wilson, W. C. "The use of exogenous plant growth regulators on citrus", Chapter 8 in Plant Growth Regulating Chemicals, Louis G. Nickell, ed. CRC Press, Boca Raton, Florida. p. 212, 1983.

METHOD OF CONTROLLING SPROUT FORMATION IN POTATOES BY SELECTIVE APPLICATION OF CHLORPROPHAM, CARVONE, BENZOTHIAZOLE AND ETHYLENE

FIELD OF THE INVENTION

This invention relates to compositions used to inhibit sprouting of tubers. More particularly, this invention relates to CIPC, benzothiazole and carvone and to methods of applying same to tubers, especially to potatoes, to inhibit sprouting during storage.

BACKGROUND OF THE INVENTION

Sprout control of harvested tubers, in particular of potatoes, is an important part of potato storage which allows for subsequent distribution to potato processors for French fry production, and to grocery stores and restaurants of a satisfactory food product months beyond harvesting, skin formation and dormancy. Potato sprout control is particularly important to maintain the desired texture and sugar content of the harvested potatoes.

In potatoes, cell division and cell elongation of the tuber buds results in formation and emanation of sprouts from the tuber buds after the potato has entered a quiescent phase of dormancy that typically follows storage at or slightly above 45° F. Although tuber sprout formation can be suppressed by storage of the tubers at lower temperatures of from 38 ° to 39° F., the lower storage temperatures cause increased reducing sugar levels in the stored potatoes. Potatoes with increased levels of reducing sugars may turn brown when french fried, thereby producing an unacceptable food product.

To inhibit sprout formation in potatoes, synthetically derived sprout inhibitors, for example, tetrachloronitrobenzene, maleic hydrazide, and isopropyl-3-chlorophenylcarbamate (CIPC) also commonly referred to as chlorpropham, have been applied. CIPC is typically applied in one or two applications to the tubers to be stored using thermal fogging techniques. Conventional thermal fogging involving the application of CIPC into a stream of hot air or onto a hot surface of up to 1000° F., to produce a CIPC aerosol.

The CIPC aerosol is circulated through potatoes piled in a potato storage building with the use of fans. Preferably the potatoes are firm rather than soft when treated with the CIPC aerosol, since a pile of softened potatoes may be substantially compressed, thereby impeding distribution of the aerosol. CIPC residue levels, will, however, typically decrease over time due to biodegradation, venting and atmospheric loss. To extend the effective sprout inhibiting capability of CIPC, further applications may be needed.

However, it is becoming increasingly desirable worldwide to decrease the application of synthetically derived substances to fruits and vegetables during growth, storage and shipping. In particular, residue levels of CIPC are subject to regulation. So, while CIPC has been utilized to inhibit sprout formation in tubers for decades, its toxicology has been questioned and it is one of a number of synthetically derived substances whose residue levels are of concern to the U.S. Environmental Protection Agency.

In order to decrease use of synthetically derived substances such as CIPC, naturally occurring biological control mechanisms and substances are actively sought. Naturally occurring sprout inhibitors are known. For example, U.S. Pat. No. 5,436,226 for NATURAL SUPPRESSION OF SPROUTING IN STORED POTATOES USING JASMONATES claims a method of inhibiting sprouting of tubers by exposure to various forms of jasmonic acid, at some of which are naturally occurring compounds.

Also by way of example, Canadian Patent No. 1,203,394 teaches the use of dimethylnaphthalene (DMN) and diisopropyinaphthalene (DIPN) as potato sprout inhibitors. However, this patent teaches the need for application of DMN and DIPN with an inert carrier which implies the utility of DMN and DIPN alone as the active ingredient. However, long term effectiveness of DMN and DIPN as tuber sprout inhibitors at lower residue levels under less than ideal circumstances has not been fully established.

By way of further example, carvone, an essential oil of caraway seeds, has been promoted as a natural sprout suppressant for potatoes. However, sprout inhibition by application of carvone does not appear to be as effective as with CIPC.

It is against this background that the significant improvements and advancements of the present invention have taken place.

OBJECTS OF THE INVENTION

It is the principal object of the present invention to manage sprouting of tubers during and after storage.

It is another object of the present invention to inhibit sprouting of tubers during storage using decreased amounts of sprout inhibitors.

It is a further object of the present invention to inhibit sprouting of tubers during storage using conventional equipment.

It is a still further object of the present invention to inhibit sprouting of tubers in accordance with the aforementioned objects in such a manner that three months after treatment, the quantity of marketable potatoes is maximized.

It is a yet further object of the present invention to stimulate the sprouting of tuber previously treated with sprout inhibition compositions to accelerate establishment and growth of tubers, and in particular, potato plants grown from seed potatoes.

SUMMARY OF THE INVENTION

In accordance with its major aspects, a composition specially adapted for inhibiting sprout formation of tubers during storage includes CIPC and either carvone or benzothiazole. In a preferred embodiment of the method of the present invention, an effective amount of a composition comprising CIPC and carvone or CIPC and benzothiazole is applied to the surface of potatoes, by, for example, by thermal fogging, to form a residue on the outer surface of the potatoes. In other preferred methods, the CIPC is applied by thermal fogging separately from the carvone or the benzothiazole to form a residual mixture on the outer surface of the potatoes. Thereafter, when planting of the treated potatoes is scheduled, the potatoes are treated with ethylene, either at the facility where they have been stored, in the truck or bin from which they will be distributed for planting, or in the field at planting, prior to covering the ethylene-treated potatoes with soil. The sprout inhibition effects of the CIPC and benzothiazole or CIPC and carvone is thereby overcome, and sprout formation accelerated beyond those potatoes not so treated with ethylene.

Employing the aforementioned method has resulted in substantial sprout control of Russet Burbank potatoes stored for approximately three months upon which an effective residue of CIPC and either carvone or benzothiazole of approximately 16.6 ppm each is applied. In addition, by subsequently overcoming the sprout inhibition by application, at planting, with ethylene, subsequent plant growth of potatoe plants grown from seed potatoes so treated is accelerated beyond plants grown from potatoes not treated with ethylene, to produce an earlier or larger potato crop than otherwise would be grown.

A more complete appreciation of the present invention and its scope can be obtained from the following detailed description of presently preferred embodiments of the invention, and the appended claims.

DETAILED DESCRIPTION OF THE INVENTION

In accordance with the present application, it has been discovered that under the particular conditions described below, benzothiazole and carvone, when mixed with isopropyl-3-chlorophenyl-carbamate (CIPC) and applied to Russet Burbank potatoes, appear to enhance the sprout inhibiting capability of reduced amounts of CIPC through 125 days after application. In view of the marginal ability of benzothiazole and carvone to inhibit sprouting of Russet Burbank potatoes under the particular conditions described below for the same period of time, the effectiveness of the combination was readily apparent. It understood that as used herein, the term benzothiazole includes all isomers, derivatives and structurally similar compounds having equivalent functionality. Similarly, the term carvone includes all isomers, derivatives and structurally similar compounds having equivalent functionality.

It has also been discovered that ethylene, when applied to CIPC treated potatoes, will controllably break the sprout inhibiting dormancy imposed by the CIPC. By so treating CIPC-treated potatoes with ethylene, the establishment of seed potatoes in the field may be accelerated, and the possibility of crop productivity maximized. Ethylene is preferably applied to potatoes at planting, it being understood that the term ethylene, as used herein, includes ethylene gas and compositions that upon application to tubers, will directly or indirectly generate ethylene gas.

To evaluate the sprout inhibiting effectiveness of CIPC and other organic compounds, including carvone and benzothiazole, alone and with CIPC, fully mature Russet Burbank potatoes were selected and treated. Russet Burbank potatoes were chosen because of their standard dormancy and sprouting qualities. Prior to treatment, the potatoes were stored in a dark, cool storage area to satisfy the dormancy period.

For each of the 21 treatments summarized in Table I, 36 mesh bags, each containing ten Russet Burbank potatoes of from 4 to 10 ounces each, were placed in a non-metallic drum having an approximate capacity of 35 gallons. The total weight of 360 potatoes in each drum averaged 140.7 pounds.

The drums containing the mesh bags of potatoes were sealed and housed in a building in which temperature was maintained throughout the testing period at approximately 46°–47° F. and approximately 96% relative humidity. Formed in each drum was an inlet in which treated and/or untreated air was introduced to the drum contents, as described below. Also formed in each drum was an outlet at the top end of the drum in which treated and/or untreated air was exhausted from the drum and thence to the outside of the building.

For all drums except the control, the ethylene-treated tubers, and the dihydroxybenzoic acid-treated tubers, CIPC, either alone or in combination with another listed organic compound, was delivered to each drum through a stinger inserted in the input port of the drum and extending the length of the drum. Treatment levels were calculated based on 16 milligrams (mg) of each of the CIPC and the other listed organic compound applied per kilogram (kg) of tubers treated, and reported in parts per million (ppm). Conventional thermal fogging techniques were used to generate the thermal fog delivered to the potatoes through the stinger. Return flow obtained from the output port was returned to the thermal fogger and recirculated through the stinger for five minutes. Each drum was then sealed for 24 hours after the application of the thermal fog. Then, for the next 125 days, 46°–47° F. air having a relative humidity of 96% was circulated through the input port of each drum and exhausted out the output port of each drum to the outside of the building, at a rate of 0.5 cubic feet per minute on a three-hour on and a three-hour off schedule.

Benzothiazole, an aromatic sulfonazole, was obtained from Sigma-Aldrich in a 96% formulation, catalog No.1-133-8. Carvone, a 6-carbon ring terpene with ketone on the ring, in particular, (2-methyl-5-(1-methylethyenyl)- 2-cylco-hexene-1 -one, was obtained from Sigma-Aldrich in a 98% formulation, catalog No. 12393-1. Cis-jasmone, a terpene with the chemical name 3- methyl-2-(2-pentenyl)-2-cylco-penten-1-one, was obtained from Sigma-Aldrich in a 90% formulation, catalog No. 277444. Limonene, a terpene, was obtained in a 97% mixture of cis and trans forms of limonene oxide, chemica name 1-methyl-4-(1-methylethenyl) cylcohexene, from Sigma-Aldrich, catalog No. 21832-4. Cinieole, a terpene with the chemical name 1,3,3-trimethyl-2- oxabicyclo-(2.2.2)octane, was obtained from Sigma-Aldrich in a 99% formulation, catalog No. C8060-1. Trans-cinnamaldehye, an aromatic aldehyde with the chemical name 3-phyl-2-propenal was obtained from Sigma-Aldrich in a 99+% formulation, catalog No. 23996-8.

For the tubers treated with CIPC and ethylene gas, the CIPC was first applied using thermal fogging techniques as described above. However, because of the potentially explosive nature of ethylene, ethylene gas was not applied using thermal fogging techniques to the CIPC tubers or to the tubers to be tested only with ethylene gas. To these tubers, ethylene gas was delivered through the vent stem from a container with a measured volume of ethylene gas.

For the tubers treated with CIPC and dihydroxybenzoic acid, the CIPC was first applied using thermal fogging techniques as described above.

However, because dihydroxybenzoic acid thermally degrades under thermal fogging conditions, dihydroxybenzoic acid was not applied using thermal fogging techniques. Instead, untreated tubers were dipped in a solution of dihydroxybenzoic acid to obtain a residue concentration of 16.6 ppm. For tubers to be tested with a combination of dihydroxybenzoic acid and CIPC, the dihydroxybenzoic acid-dipped tubers where then fogged with CIPC.

Dihydroxybenzoic acid, an aromatic benzoic, was obtained from Sigma-Aldrich in a 2,6-dihydroxyybenzoic acid 98% formulation, catalog No. D10960.

At 125 days after treatment, a sample of six of the 36 bags from each drum were removed, and the sixty total tubers from the six bags examined.

Each eye on each tuber was evaluated for sprout development. No sprout development is preferred, and tubers showing no sprout development are suitable for fresh pack.

As used herein, the term fresh pack indicates potatoes which meet conventional standards set by groceries for the grade of potatoes sold as baking potatoes. Tubers exhibiting sprout peeping wherein tissue swelling is detected and free tissue is evident but no sprouts are measured, are suitable for fresh pack. Tubers having sprouts, which, on average are greater than 1 mm are generally unacceptable for fresh pack.

Data obtained from evaluation of the potatoes at 125 days after treatment is summarized in Table I.

TABLE I

| Treatment | Level | 125 DAYS AFTER TREATMENT | |
|---|---|---|---|
| | | % suitable for fresh pack | % unsuitable for fresh pack |
| Control | 0 ppm | 2% | 98% |
| Control | 0 ppm | 3% | 97% |
| CIPC | 16.6 ppm | 52% | 48% |
| CIPC | 16.6 ppm | 59% | 41% |
| CIPC | 16.6 ppm | 21% | 79% |
| Benzothiazole | 16.6 ppm | 5% | 95% |
| Benzothiazole +CIPC | 16.6 ppm 16.6 ppm | 72% | 28% |
| Carvone | 16.6 ppm | 0% | 100% |
| Carvone +CIPC | 16.6 ppm 16.6 ppm | 57% | 43% |
| Cineole | 16.6 ppm | 7% | 93% |
| Cineole +CIPC | 16.6 ppm 16.6 ppm | 39% | 61% |
| Cinnamaldehyde | 16.6 ppm | 0% | 100% |
| Cinnamaldehyde +CIPC | 16.6 ppm 16.6 ppm | 2% | 98% |
| Dihydroxybenzoic | 16.6 ppm | 2% | 98% |
| Dihydroxybenzoic +CIPC | 16.6 ppm 16.6 ppm | 3% | 97% |
| Ethylene | 16.6 ppm | 3% | 97% |
| Ethylene +CIPC | 16.6 ppm 16.6 ppm | 10% | 90% |
| Limonene | 16.6 ppm | 3% | 97% |
| Limonene +CIPC | 16.6 ppm 16.6 ppm | 0% | 100% |
| Jasmone | 16.6 ppm | 1% | 99% |
| Jasmone +CIPC | 16.6 ppm 16.6 ppm | 17% | 83% |

As is summarized in Table I above, at 125 days after treatment, on average 43% (i.e., (51%+58%+21%)/3) of the tubers treated with CIPC alone at a 16.6 ppm residue level exhibited no sprout development beyond peeping, and thus were suitable for fresh pack. Conversely, on average, 57% of tubers so treated were unsuitable for fresh pack sale.

In contrast, as is also summarized in Table I, on average, only 1.5% (i.e., (2%+1%)/2) of the untreated control tubers showed no sprout development or peeping. Therefore, on average, 1.5% of the untreated control tubers were suitable for fresh pack at 125 days after treatment, making 98% of untreated control tubers unsuitable for fresh pack sale.

Only 5% of the tubers treated with benzothiazole showed no sprout development or peeping. Accordingly, only 5% of the tubers treated with benzothiazole were suitable for fresh pack at 125 days after treatment, making 95% of the tubers treated with benzothiazole alone unsuitable for fresh pack sale.

In contrast, 71% of the tubers treated with benzothiazole and CIPC showed no sprout development or peeping. Accordingly, 71 % of the tubers treated with benzothiazole and CIPC were suitable for fresh pack at 125 days after treatment, and thus 29% of the tubers treated with benzothiazole and CIPC were unsuitable for fresh pack sale.

None of the tubers treated with 16.6 ppm carvone showed no sprout development or peeping. Accordingly, none of the tubers treated with this level of carvone were suitable for fresh pack at 125 days after treatment, making 100 f the tubers treated with 16.6 ppm carvone alone unsuitable for fresh pack sale.

Approximately 55% of the tubers treated with carvone and CIPC showed no sprout development or peeping, and thus, 55% of the tubers treated with carvone and CIPC were suitable for fresh pack at 125 days after treatment. Conversely, 475 of the tubers treated with carvone and CIPC were unsuitable for fresh pack sale.

In contrast, in all tests where tubers were treated with cineole, cinnamaldehyde, dihydroxybenzoic, ethylene, limonene or jasmone, alone or in combination with CIPC, and in accordance with the method described herein, at 125 days 61 % to 100% of the tubers were unsuitable for fresh pack sale. It can be seen from a review of Table I that at the residue levels tested, the sprout inhibition functionality of CIPC was not universally enhanced when applied in conjunction with other compounds.

Moreover, in addition to utilizing thermal fogging techniques to produce and apply the improved sprout inhibiting compositions of the present invention, other conventional application methods may be employed. For example, potatoes may be dipped into a solution or solutions comprising the improved sprout inhibiting composition of the present invention. Also by way of example, the improved sprout inhibiting compositions of the present invention may be sprayed in aerosol form at temperatures less than the elevated temperatures utilized with thermal fogging, for example at ambient temperatures. By way of further example, dusts of dried sprout inhibiting compositions may be applied for some of the organic compounds identified above, with or without the addition of dyes to improve product acceptability.

At the 125 days after treatment, average sprout length measurements were determined for the untreated control tubers and for tubers treated CIPC, ethylene, and CIPC plus ethylene. The data relating thereto is summarized in Table II.

TABLE II

| Treatment | Level | AVERAGE SPROUT LENGTH 125 DAYS AFTER TREATMENT |
|---|---|---|
| Control | 0 ppm | 4.65 cm |
| CIPC | 16.6 ppm | 1.80 cm |
| Ethylene | 16.6 ppm | 4.78 cm |
| Ethylene +CIPC | 16.6 ppm 16.6 ppm | 3.07 cm |

Clearly, the ethylene was able to overcome a portion of the sprout inhibition functionality of the CIPC. Most importantly, the average thickness of sprouts of potatoes treated with ethylene alone and ethylene and CIPC was 1.5 times thicker than the thickness of sprouts from the untreated control tubers. The greater average thickness is indicative of sprout vigor which is not evident from sprout length measurements alone.

Presently preferred embodiments of the present invention and many of its improvements have been described with a degree of particularity. It should be understood that this description has been made by way of preferred examples, and that the invention is defined by the scope of the following claims.

What is claimed is:

1. A method of controlling sprout growth of tubers comprising the steps of:

treating the tubers with at least 16.6 ppm CIPC to form a residue thereon in an amount effective to inhibit sprout formation of said tubers;

treating the tubers with at least 16.6 ppm carvone to form a residue thereon; and storing the treated tubers.

2. The method of claim 1 further comprising the step of treating said stored tubers with ethylene to stimulate sprout formation thereof.

3. A method of inhibiting sprout formation in tubers during storage, comprising the steps of:

provividing a composition comprising CIPC and benzothiazole to form a sprout inhibiting composition;

applying an effective amount of the sprout inhibiting composition to the outer surface of said tubers to form treated tubers; and storing said treated tubers.

4. A method of wherein the controlling sprout growth of tubers comprising the steps of:

treating the tubers with CIPC to form a residue thereon in an amount effective to inhibit sprout formation of said tubers;

treating the tubers with benzothiazole to form a residue thereon; and storing the treated tubers.

5. The method of claim 4 further comprising the step of treating said stored tubers with ethylene to stimulate sprout formation thereof.

6. A method of controlling sprout formation in tubers comprising the steps of:

treating said tubers with CIPC to form a residue thereon in an amount effective to inhibit sprout formation of said tubers and to impose a CIPC-induced dormancy;

storing said treated tubers; and treating said stored tubers with ethylene in an amount equal to or greater than the CIPC effective amount to stimulate sprout growth of said stored tuber and to break the CIPC-induced dormancy.

7. The method of claim 6 further comprising the step of planting said treated tubers.

\* \* \* \* \*